US007741602B2

(12) United States Patent
Benner et al.

(10) Patent No.: US 7,741,602 B2
(45) Date of Patent: Jun. 22, 2010

(54) PHASE CONTRAST ELECTRON MICROSCOPE

(75) Inventors: Gerd Benner, Aalen (DE); Marko Matijevic, Nürtingen (DE)

(73) Assignee: Carl Zeiss NTS GmbH, Oberkochen (DE)

( * ) Notice: Subject to any disclaimer, the term of this patent is extended or adjusted under 35 U.S.C. 154(b) by 405 days.

(21) Appl. No.: 11/717,201

(22) Filed: Mar. 13, 2007

(65) Prior Publication Data

US 2007/0284528 A1 Dec. 13, 2007

(30) Foreign Application Priority Data

Mar. 14, 2006 (DE) ...................... 10 2006 011 615

(51) Int. Cl.
*G01N 23/00* (2006.01)

(52) U.S. Cl. ...................... 250/311; 250/306; 250/310; 250/396 R; 250/492.1; 250/492.3

(58) Field of Classification Search ................ 250/306, 250/307, 310, 311, 396 R, 492.1, 492.2, 492.22, 250/492.23, 492.3
See application file for complete search history.

(56) References Cited

U.S. PATENT DOCUMENTS

| | | | | |
|---|---|---|---|---|
| 2,802,110 | A | 8/1957 | Kazato et al. | |
| 3,493,287 | A * | 2/1970 | Lohmann | 359/566 |
| 3,566,109 | A * | 2/1971 | Heidenreich | 250/307 |
| 3,596,090 | A * | 7/1971 | Hoppe | 250/311 |
| 4,953,188 | A * | 8/1990 | Siegel et al. | 378/43 |
| 5,013,913 | A | 5/1991 | Benner | |
| 5,550,887 | A * | 8/1996 | Schmal et al. | 378/43 |
| 5,814,815 | A * | 9/1998 | Matsumoto et al. | 250/311 |
| 6,531,698 | B1 | 3/2003 | Benner | |
| 6,674,078 | B2 * | 1/2004 | Nagayama et al. | 250/311 |
| 6,744,048 | B2 * | 6/2004 | Hosokawa et al. | 250/311 |
| 6,797,956 | B2 | 9/2004 | Benner | |
| 2002/0011566 | A1 * | 1/2002 | Nagayama et al. | 250/311 |
| 2002/0148962 | A1 * | 10/2002 | Hosokawa et al. | 250/311 |
| 2002/0153484 | A1 * | 10/2002 | Kaneyama | 250/311 |
| 2003/0043458 | A1 * | 3/2003 | Minobe et al. | 359/386 |
| 2003/0127595 | A1 * | 7/2003 | Nakamura et al. | 250/311 |
| 2003/0132383 | A1 * | 7/2003 | Benner | 250/311 |

FOREIGN PATENT DOCUMENTS

WO WO 2005/022582 3/2005

* cited by examiner

*Primary Examiner*—Nikita Wells
*Assistant Examiner*—Michael J Logie
(74) *Attorney, Agent, or Firm*—Walter Ottesen

(57) ABSTRACT

A phase contrast electron microscope has an objective (8) with a back focal plane (10), a first diffraction lens (11), which images the back focal plane (10) of the objective (8) magnified into a diffraction intermediate image plane, a second diffraction lens (15) whose principal plane is mounted in the proximity of the diffraction intermediate image plane and a phase-shifting element (16) which is mounted in or in the proximity of the diffraction intermediate image plane. Also, a phase contrast electron microscope has an objective (8) having a back focal plane (10), a first diffraction lens (11), a first phase-shifting element and a second phase-shifting element which is mounted in or in the proximity of the diffraction intermediate image plane. The first diffraction lens (11) images the back focal plane of the objective magnified into a diffraction intermediate image plane and the first phase-shifting element is mounted in the back focal plane (10) of the objective (8). With the magnified imaging of the diffraction plane by the diffraction lens, the dimensional requirements imposed on the phase plate having the phase-shifting element are reduced.

18 Claims, 7 Drawing Sheets

PHASE CONTRAST ELECTRON MICROSCOPE

CROSS REFERENCE TO RELATED APPLICATION

This application claims priority of German patent application no. 10 2006 011 615.1, filed Mar. 14, 2006, the entire content of which is incorporated herein by reference.

FIELD OF THE INVENTION

The invention relates to a phase contrast electron microscope and especially a phase contrast transmission electron microscope.

BACKGROUND OF THE INVENTION

Electron microscope specimens are, as a rule, phase objects which generate only a very slight amplitude contrast in a transmission electron microscope because of the high electron energy in the range of 100 keV and higher. For this reason, in a conventional transmission electron microscope, objects of this kind generate a contrast only when utilizing the phase-shifting effect of the spherical aberration of the transmission electron microscope and are therefore imaged with correspondingly little contrast in a conventional transmission electron microscope. The introduction of a phase plate into the back focal plane of the objective of the transmission electron microscope therefore provides a large increase in contrast in a manner similar to the generation of a phase contrast in phase objects according to Zernicke in the optical microscopy. However, the dimensions required in a transmission electron microscope are problematic. Especially when the so-called unscattered ray (that is, only the ray which is undiffracted at the specimen) is to be shifted in phase, but the ray, which is diffracted at the specimen into the first order or higher orders, is intended to be uninfluenced by the phase plate, the small diameter of the unscattered ray of less than 1 μm imposes considerable requirements on the technology because, for the phase plate, freedom from contamination, freedom of charging and dielectric strength are required.

For generating the phase-shifting effect, basically two starting points are known, namely: for the first starting point, the phase plate is realized as a correspondingly small configured electrostatic lens which imparts a phase shift only to the unscattered ray but leaves the higher diffracting orders entirely or substantially uninfluenced. For the second starting point, a thin foil is used which is substantially transparent for electrons of the electron energy used in the transmission electron microscope and which has the required structure. For the second starting point, the inherent electrostatic potentials of the material are used in order to impart the desired phase shift onto the unscattered ray or onto the scattered electron rays. The first starting point has the disadvantage that the small electrostatic lens perforce requires outer holding structures which interrupt regions wherein the paths of the electrons run which are diffracted into high diffraction orders whereby important information is lost for the generation of images. With respect to the latter, the second starting point has the disadvantage that the higher orders of diffraction, which are anyway very weak compared to the unscattered ray, are additionally weakened by the unavoidable material absorption of the foil. Because of these technological problems, no phase contrast electron microscopes with phase-shifting elements directly in the back focal plane of the objective lens could, up to now, be successfully established in the marketplace as commercial products even though the basics for the generation of phase contrast have been known for more than fifty years.

Phase contrast electron microscopes are described in U.S. Pat. Nos. 6,744,048 and 6,797,956 which are incorporated herein by reference.

In U.S. Pat. No. 6,744,048, the suggestion is made to image the back focal plane of the objective by a lens system and to arrange the phase-shifting element in the image plane of the diffraction plane of the objective with the image plane being generated by the lens system.

SUMMARY OF THE INVENTION

It is an object of the invention to provide a phase contrast electron microscope wherein the dimensional requirements on the phase-shifting element are reduced. Another object of the invention is to avoid information loss in a phase contrast electron microscope.

The first object is achieved with a phase contrast electron microscope which includes: an objective mounted on the optical axis and defining a back focal plane; a first diffraction lens for imaging the back focal plane into a diffraction intermediate image plane; a second diffraction lens having a principal plane disposed in the vicinity of the diffraction intermediate image plane; and, a phase-shifting element mounted in or near the diffraction intermediate image plane.

The second object is realized with a phase contrast electron microscope including: an objective mounted on the optical axis and defining a back focal plane; a diffraction lens for imaging the back focal plane into a diffraction intermediate image plane; a first phase-shifting element mounted in the back focal plane; and, a second phase-shifting element mounted in or near the diffraction intermediate image plane.

According to a first aspect of the invention, a phase contrast electron microscope has an objective having a back focal plane and a first diffraction lens which images the back focal plane of the objective magnified into a diffraction intermediate image plane. In the propagation direction of the electrons, a second diffraction lens follows the first diffraction lens and has a principal plane which is arranged in the vicinity of the diffraction intermediate image plane. A phase-shifting element is mounted in or near the diffraction intermediate image plane.

According to a second aspect of the invention, a phase contrast electron microscope has an objective having a back focal plane and a first diffraction lens which images the back focal plane of the objective into a diffraction intermediate image plane. A first phase-shifting element is mounted in or near the back focal plane of the objective and a second phase-shifting element is mounted in or near the diffraction intermediate image plane. The imaging of the back focal plane is effected with the first diffraction lens and is imaged, preferably magnified, into the diffraction intermediate image plane.

The diffraction plane of the objective is imaged magnified into a diffraction intermediate image plane. For this reason, the phase-shifting element can be configured to be correspondingly geometrically larger so that the dimensional requirements imposed on the phase-shifting element are correspondingly reduced. At the same time, the blanking out of electrons with the hardware of the phase plate, especially electrodes and support elements, is reduced because the dimensions of these parts can remain the same. Furthermore, it can simultaneously be ensured that no deterioration of resolution occurs because of the aberrations of the additional diffraction lenses and the image of the diffraction plane behind the system of the diffraction lenses can lie clearly rearward of the image planes which are conjugated to the object plane of the objective.

Because, according to the first aspect of the invention, the principal plane of the second diffraction lens lies in or near the diffraction intermediate image plane, the second diffraction lens has an almost exclusive influence on the position of the image plane, which is conjugated to the object plane of the objective, and virtually no influence on the additional imaging of the diffraction intermediate image plane. The required structural length increase can thereby be kept low.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
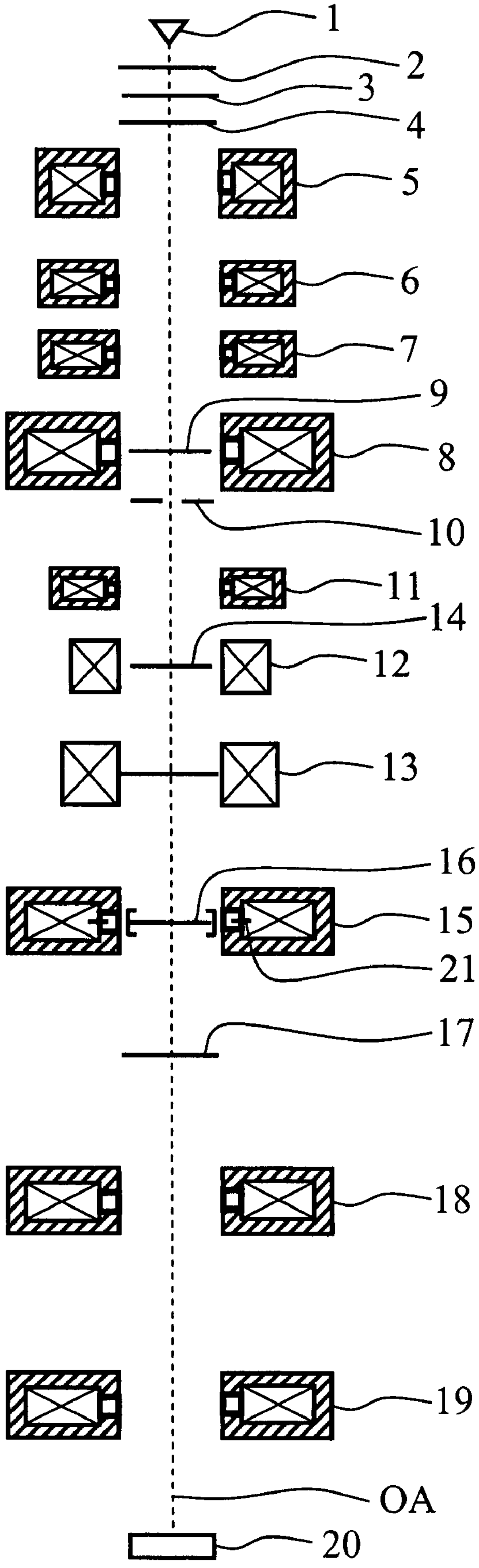
FIG. 1 is a schematic, in section, of a phase contrast transmission electron microscope.

The transmission electron microscope of FIG. 1 includes an electron source 1, for example, a thermal field emission source. An extraction electrode 2 follows the electron source 1 and this extraction electrode has a potential which draws electrons from the electron source 1. The extraction electrode 2 is followed by one or several focusing electrodes 3 in order to optically fix the location of the source position and one or several anodes 4. Because of the potential of the anode 4, the electrons, which emanate from the electron source 1, are accelerated to the desired electron energy of 100 keV or more.

A multi-stage condenser follows the anode in the direction of movement of the electrons. In the embodiment shown, the condenser has three individual magnet lenses (5, 6, 7) and the entrance end part of the condenser-objective single-field lens 8. With a condenser of this kind, the illumination aperture as well as the field of the object plane 9 can be independently adjusted by a corresponding adjustment of the lens currents of the magnetic lenses (5, 6, 7, 8). The field of the object plane 9 is the field illuminated by the electron beam and the object plane 9 lies in the principal plane of the condenser-objective single-field lens 8. U.S. Pat. No. 5,013,913 is incorporated herein by reference with respect to the beam guidance in the condenser for different illumination fields and apertures. In lieu of a four-stage condenser, a simple condenser can, however, be provided as shown, for example, in U.S. Pat. No. 6,531,698 incorporated herein by reference.

In the condenser-objective single-field lens 8, the prefield functions as a last condenser lens and the back field functions as an objective lens. The object plane lies approximately at the elevation of the pole piece gap of the condenser-objective single-field lens 8. A specimen manipulator (not shown) in the form of a goniometer is mounted in the object plane 9. The specimen manipulator is guided through the pole piece of the condenser-objective single-field lens 8.

In lieu of the condenser-objective single-field lens, also other objective lenses can be provided.

A first diffraction lens 11 follows the condenser-objective single-field lens 8 and is likewise configured as a magnet lens. This first diffraction lens 11 images the back focal plane or diffraction plane 10 of the condenser-objective single-field lens 8 magnified into a diffraction intermediate image plane 21. At the same time, the first diffraction lens 11 generates a real intermediate image 14 of the object plane 9. A first deflection system 12 is mounted in the plane of the intermediate image 14 generated by the first diffraction lens 11. A second deflection system 13 follows this first deflection system 12 and thereafter, a second diffraction lens 15. The diffraction intermediate image plane 21 then lies simultaneously in or near the principal plane of the second diffraction lens 15.

A phase plate 16 is mounted in the diffraction intermediate image plane 21. The image of the diffraction plane 10 of the objective lens or of the imaging part of the field of the condenser-objective single-field lens 8 is magnified because of the imaging scale of the image generated by the first diffraction lens 11. For this reason, the diameter of the phase plate 16 is magnified by this imaging scale relative to an arrangement of the phase plate 16 directly in the back focal plane 10 of the objective lens. The other dimensions of the phase plate 16, such as the width of the holding elements (22, 27) and the radial width (difference between inner and outer diameters) of the annularly-shaped electrode can, in contrast, stay dimensioned the same so that the blanking of electrons by these components is overall reduced.

The magnification with which the diffraction plane 21 is imaged into the diffraction intermediate image plane should be greater by a factor of two, preferably by a factor of three. The magnification with which the diffraction plane 21 is imaged into the diffraction intermediate image plane should not exceed a tenfold magnification and should preferably lie between a threefold magnification and a sevenfold magnification.

The second diffraction lens 15 is so mounted that its principal plane lies in or near the diffraction intermediate image plane. For this reason, the second diffraction lens 15 has no influence or no significant influence on the further imaging of the diffraction intermediate image plane 21. This second diffraction lens 15 primarily images the intermediate image 14 of the object plane 9 into the entrance image plane 17 of the projective system (18, 19). In this way, a suitably long distance of the next-following image planes of the object plane 9 and the diffraction plane 10 is ensured. The projective system (18, 19) then generates a greatly magnified image on a detector 20 of the specimen arranged in the object plane 9 and imaged into the entrance image plane 17 of the projective system (18, 19).

In FIG. 1, the reference characters OA identify the optical axis of the entire electron optical system.

The lateral position of the image of the diffraction plane 10 of the objective can be finely adjusted relative to the phase plate 16 with the aid of the deflection systems (12, 13) between the first diffraction lens 11 and the second diffraction lens 15. The first deflection system is mounted or operates in the plane in which the intermediate image 14 of the object plane arises. For this reason, a deflection, which is effected by this first deflection system, has no influence on the lateral position of the image of the object plane which arises in the entrance image plane 17 of the projective system; rather, the first deflection system only shifts the position of the diffraction image relative to the phase plate 16.

Figure 2:
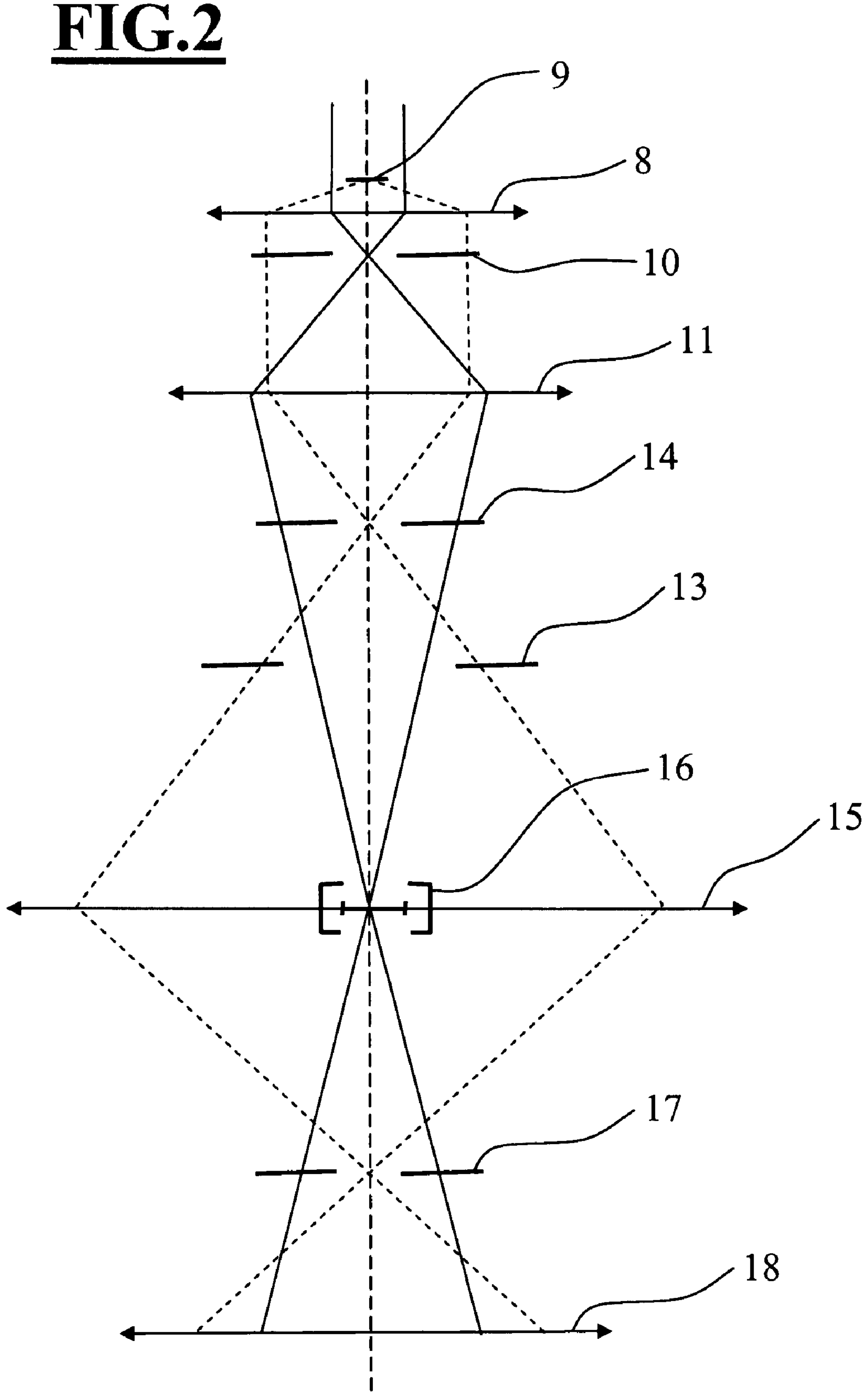
FIG. 2 shows the beam paths in the electron microscope of FIG. 1 in a first operating mode.

The imaging characteristics described above between the objective lens 8 and the first projective lens 18 are shown in FIG. 2 with respect to the beam paths. The solid lines show the beam paths for the electrons which emanate parallel to the optical axis OA from the object plane 9 (the so-called illumination beam path or pupil beam path) and the broken lines show the beam paths for the electrons which leave from the object plane 9 on the optical axis OA at an angle to the optical axis OA (the so-called imaging beam path).

Figure 3:
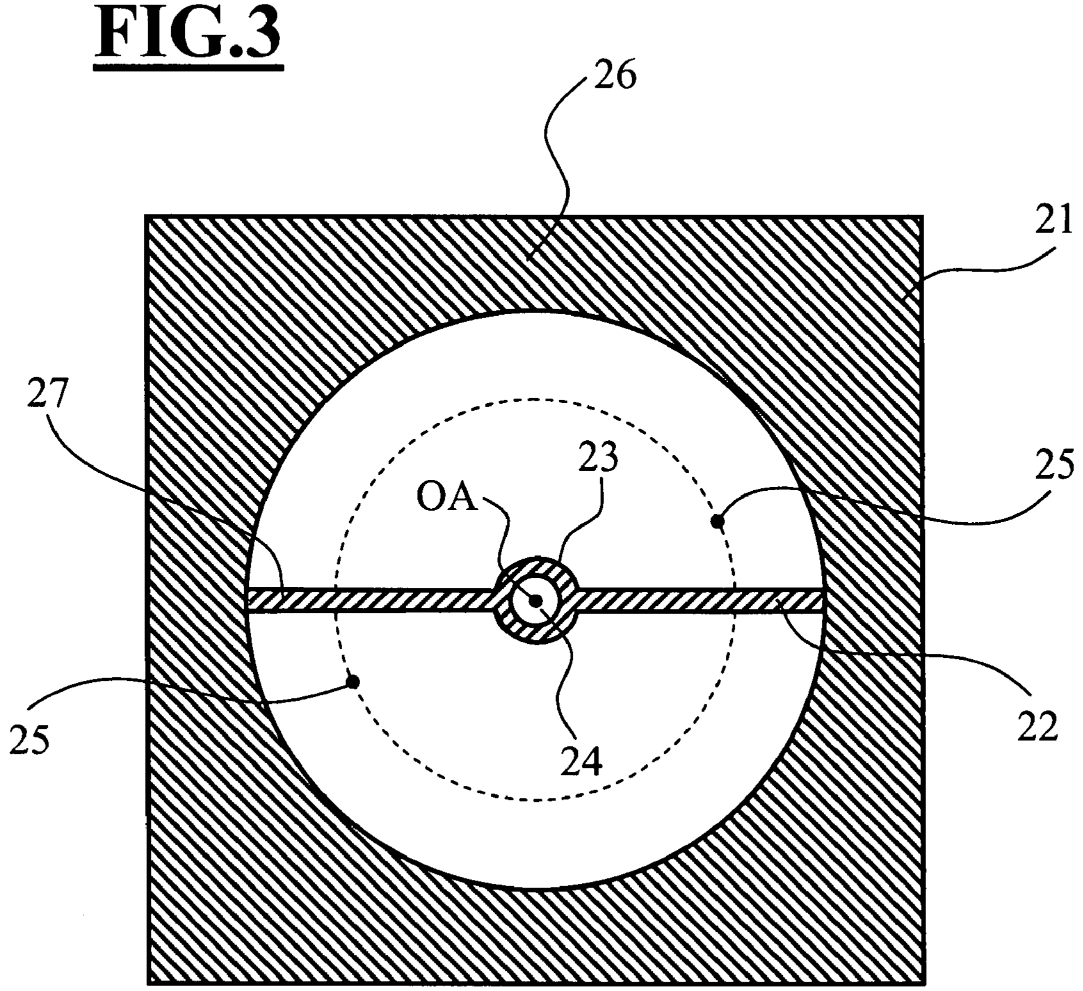
FIG. 3 is a plan view of an electrostatic phase plate in an electron microscope of FIG. 1.

An electrostatic phase plate 16 is shown in plan view in FIG. 3. The phase plate 16 has an outer carrier 21 having a round aperture 26 with the carrier 21 being opaque to electrons. An annular electrode 23 having a central annular opening 24 is mounted in the aperture 26 centered on the optical axis OA. The annularly-shaped electrode 23 is connected to the carrier 21 via two or three thin holding elements (22, 27). By applying an electrostatic potential to the annularly-shaped electrode, a phase shift is imparted to the unscattered ray or the rays which are not diffracted in the object plane 9 while the rays are uninfluenced which are scattered or diffracted in the object plane at higher orders. The unscattered ray passes through the annular opening. Reference can be made to U.S. Pat. No. 6,797,956 with respect to details as to the configuration of the phase plate 16. U.S. Pat. No. 6,797,956 is incorporated herein by reference.

By changing the excitation of the second diffraction lens 15, the orientation of the diffraction image relative to the phase plate 16 can be changed by the image rotation effected by this diffraction lens 15. In this way, diffraction spots 25, which are essential for the image formation and which impinge on the holding elements (22, 27), can be moved on a circular path indicated by the circle drawn by a dotted line circle and can thereby be rotated into a region wherein they can pass through the phase plate undisturbed by the holding elements (22, 27).

Figure 4:
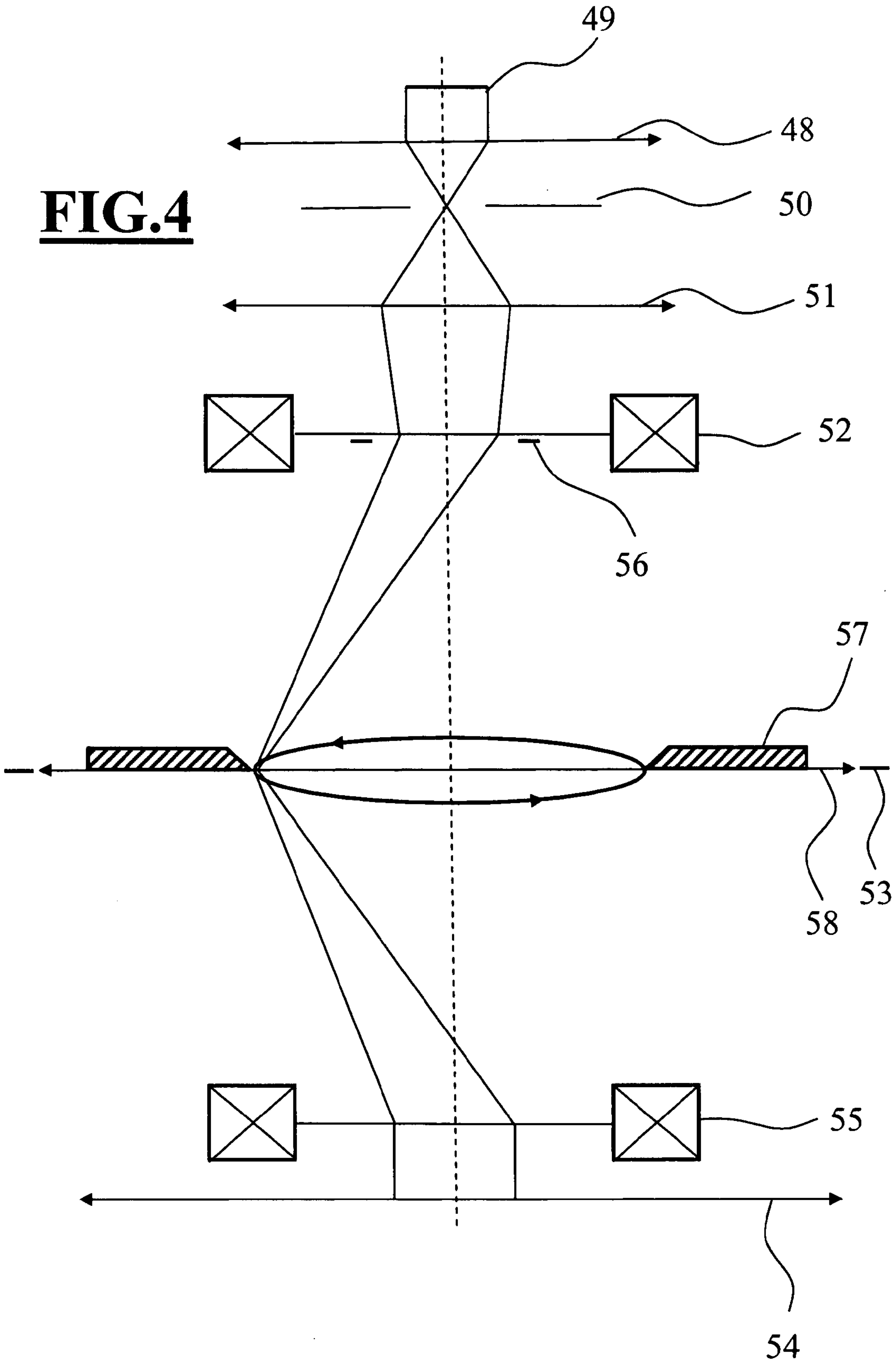
FIG. 4 shows the beam paths in the phase contrast electron microscope having a conical illumination aperture.

FIG. 4 shows the beam path in the case of the generation of a phase contrast with a conical illumination that is disclosed in U.S. Pat. No. 6,797,956. The unscattered ray is undiffracted in the object plane 49 and is focused in the diffraction plane 50 of the objective 48 and is imaged into the diffraction intermediate image plane 53 by the first diffraction lens 51. The first deflection system 52 in the vicinity of the intermediate image plane 56 guides the beam in an annular shape across the phase-shifting regions of an annularly-shaped phase plate 57 in the diffraction intermediate image plane 53. The second diffraction lens 58 has a principal plane which lies in or in the vicinity of the diffraction intermediate image plane 53 and generates an intermediate image of the object plane 49 in the entrance image plane of the first projective lens 54. A further deflection system 55 is arranged in the entrance image plane of the first projective lens 54 and is operated in synchronism with the first deflection system 52. With this deflection system 55, the ray can again be deflected back onto the optical axis in the entrance image plane of the first projective lens 54.

An annularly-shaped phase plate is mounted in the diffraction intermediate image plane 53 and with this phase plate, a phase shift is imparted to the unscattered ray guided on a circular path while the electrons, which pass farther from the edge of the center opening of the phase plate, remain uninfluenced by the phase plate with these electrons having been diffracted in the object plane 49 into higher diffraction orders. A phase contrast again arises via interference of these higher diffraction orders with the phase-shifted unscattered ray.

Figure 5:
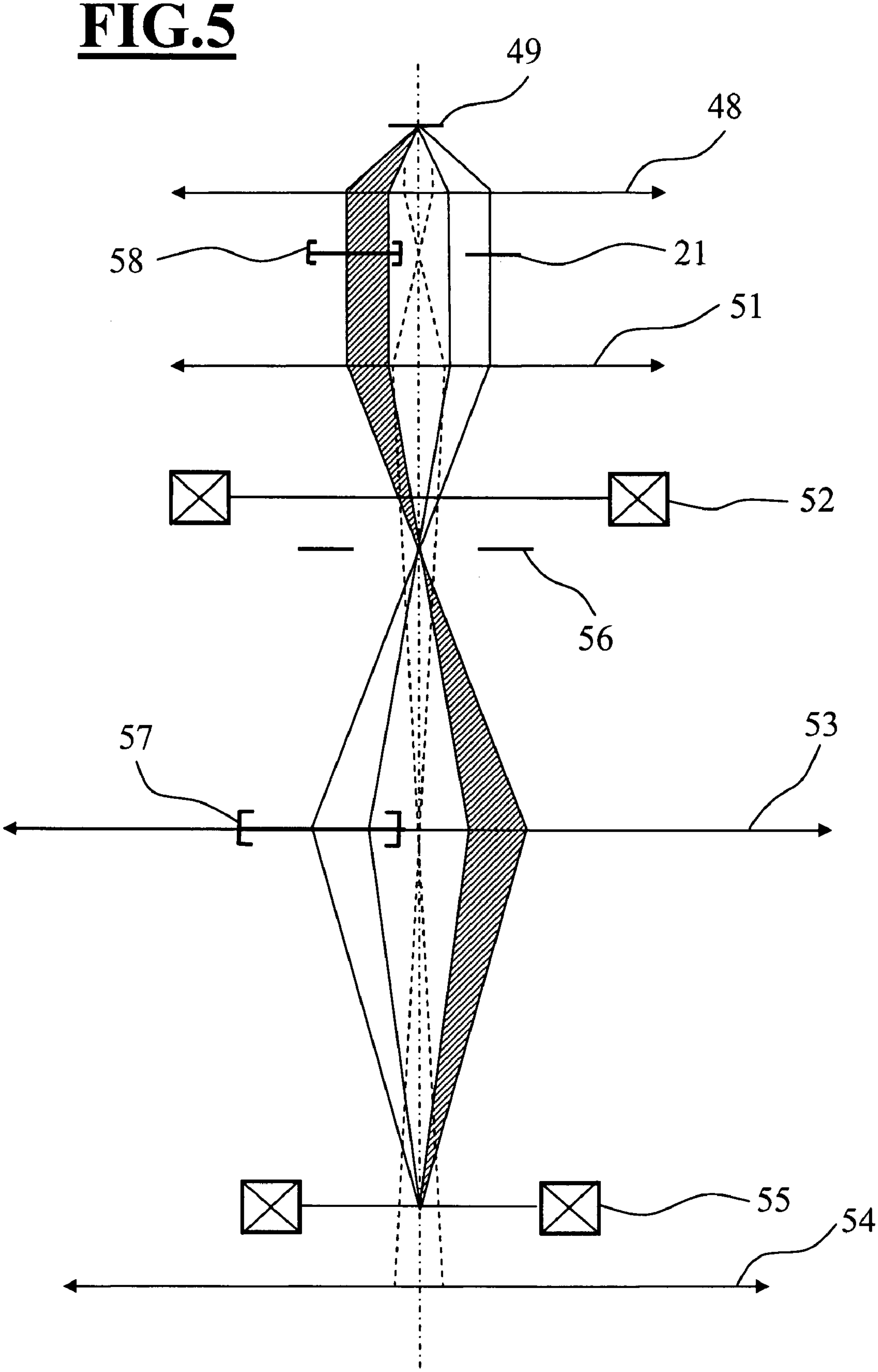
FIG. 5 shows the beam paths in a system having two phase plates which are mounted in planes conjugated to each other.

The arrangement of FIG. 5 is built up essentially in the manner of the arrangement shown in FIG. 4. However, the arrangement of FIG. 5 includes two phase plates. The first phase plate 58 is mounted in the diffraction plane 21 of the objective lens and a second phase plate 57 is mounted in the image plane of the first diffraction lens 51 conjugated to the diffraction plane 15. The first diffraction lens 51 lies in or near the principal plane of the second diffraction lens 53. As in the embodiment described above, the second diffraction lens images a real intermediate image of the object plane 49 into the entrance image plane of the projective system 54. The real intermediate image of the object plane 49 lies between the first and second diffraction lenses (51, 53).

The two phase plates (57, 58) are so configured that they each influence different spatial regions of the diffraction images which spatial regions are complementary to each other. As indicated in FIG. 5, the phase plate 58, which is mounted in the diffraction plane 21 of the objective, generates a phase shift in the beam conical segment shown hatched in FIG. 5 while the second phase plate 57 generates a phase shift in the non-hatched beam conical segment. The second phase plate 57 is mounted in the diffraction intermediate image plane. The phase shift takes place sequentially in the two mutually conjugated diffraction images so that, from the two contributions together, the wanted phase shift results between the unscattered ray and the diffracted rays. This offers in principle the possibility of realizing matter-free and aberration-free electrostatic phase plates. Furthermore, the two phase plates (57, 58) can each be so configured that possibly present holding elements in total cannot negatively influence the image generation. If only the scattered electrons experience a phase shift of n with a half-planar phase plate, then a differential interference contrast can be generated.

Figure 6:
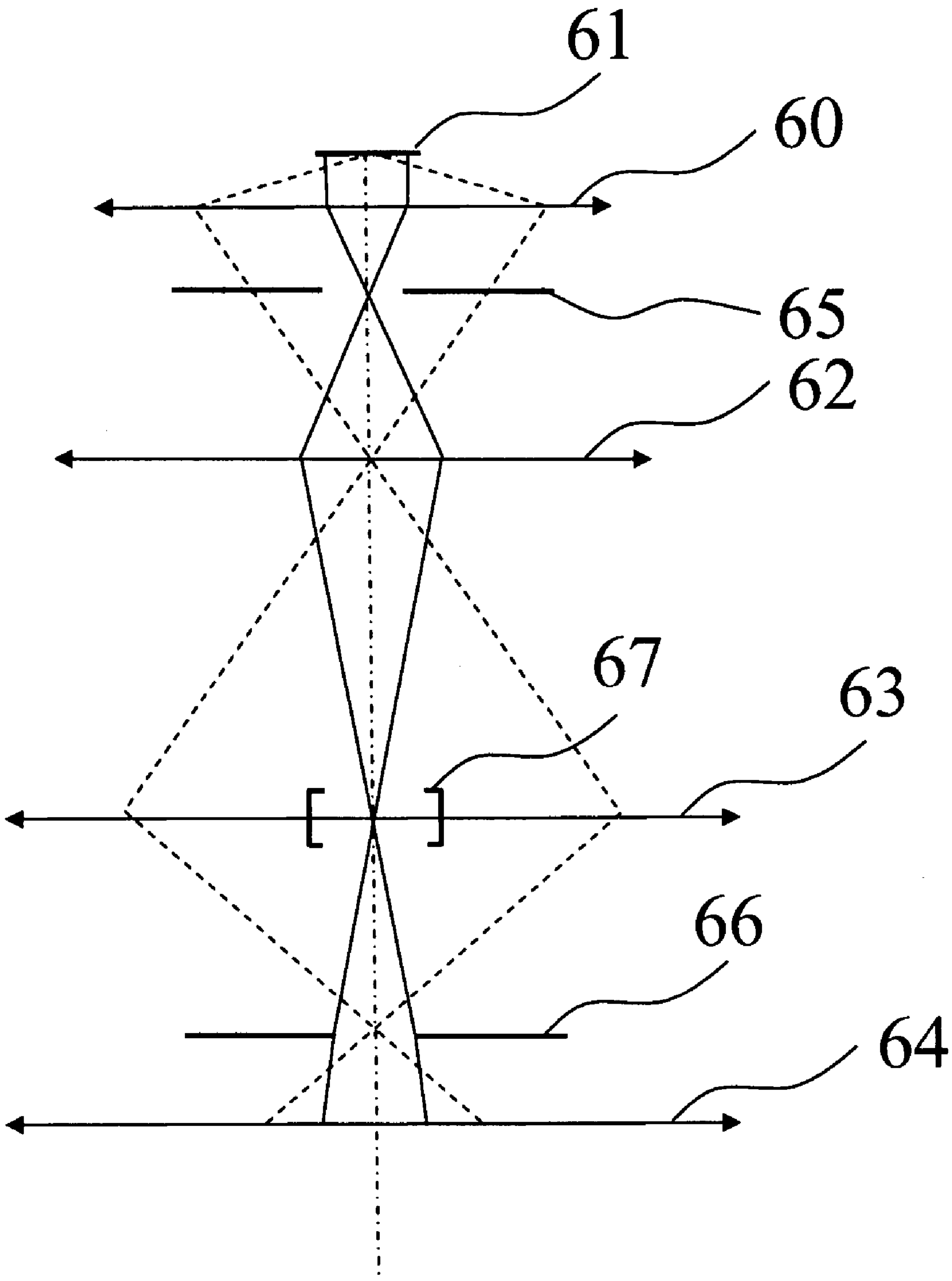
FIG. 6 shows the beam paths in the electron microscope of FIG. 1 in a second operating mode; and, FIG. 7 shows the beam paths in the electron microscope of FIG. 1 during operation as a Lorentz microscope as well as with low magnification.

In FIG. 6, a somewhat different beam guidance is shown with the embodiment already described with respect to FIGS. 1 and 2. The essential difference is that the objective lens 60 is so highly excited that it generates an intermediate image of the object plane 61 already in or near the principal plane of the first diffraction lens 62. The first diffraction lens 62, in turn, images the diffraction plane 65 of the objective lens 60 into or in the vicinity of the principal plane of the second diffraction lens 63 so that there again a diffraction intermediate image plane arises. The phase-shifting element 67 is then again mounted in the diffraction intermediate image plane. As in the embodiment in FIG. 2, the second diffraction lens 63 images the intermediate image of the object plane 61 into the entrance image plane 66 of the downstream projective system 64 with this intermediate image arising in the principal plane or in the proximity of the principal plane of the first diffraction lens.

Figure 7:
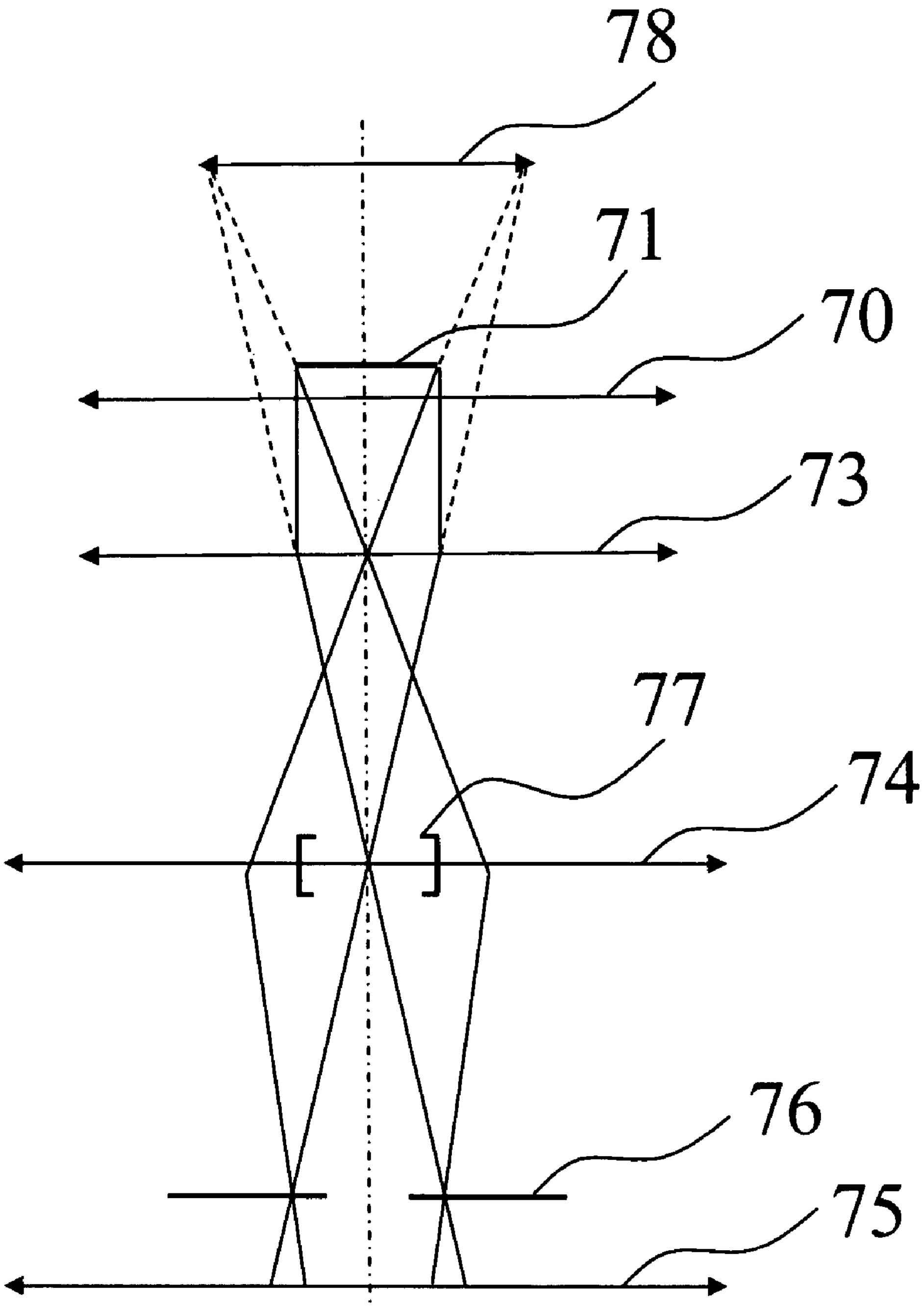

In FIG. 7, the beam path is shown which is realized for operation of the system as a Lorentz microscope or with low magnification. During operation as a Lorentz microscope, the objective lens 70 is switched off and with low magnification (so-called low-mag-mode), the objective lens is only slightly excited. The excitation of the first diffraction lens 73 is so selected that its focal plane lies in the principal plane of the second diffraction lens 74. The phase plate 77 is, in turn, mounted in the principal plane of the second diffraction lens. The second diffraction lens 74 generates a real image of the virtual image 78 of the object plane 71 in the entrance image plane 76 of the downstream projective system 75, the virtual image being generated by the first diffraction lens 73. The projective system 75 then generates an image magnified by up to a factor of 10,000 of the object positioned in the object plane 71. This beam guidance thereby makes possible a maximum magnification approximately greater by a factor of 5 compared to a conventional low-mag magnification.

With respect to the required dimensions in the beam guidance of FIG. 2, the following can be estimated: for a focal length of the objective lens 8 of approximately 3 mm and a desired telescope magnification by a factor of 10 (because the objective lens 8 and the first diffraction lens 11 are operated telescopically), there results for the first diffraction lens 11 a focal length of approximately 30 mm. It can be shown that for telescope systems of this kind, the increase of the spherical aberration is negligible compared to a system only with the objective lens.

Should the diffraction intermediate image plane be magnified approximately by the factor of 5 compared to the diffraction plane 10 of the objective lens 8, then the first diffraction lens 11 has to have a distance of approximately 36 mm from the rearward diffraction plane 10 of the objective lens 8 and a distance of 180 mm is required between the first diffraction lens 11 and the second diffraction lens 15. The second diffraction lens 15 images the intermediate image of the object plane 9 into the entrance image plane 17 of the projective system 18 with low magnification with the intermediate image arising in the back focal plane 14 of the first diffraction lens 11. For this reason, a required distance of approximately 150 mm results between the second diffraction lens 15 and the entrance image plane 17 of the projective system 18 for a focal length of the second diffraction lens 15 of approximately 75 mm. In total, there results a structural length increase of approximately 260 mm compared to an arrangement wherein the objective lens 8 directly generates a real intermediate image in the entrance image plane of the projective system.

It is understood that the foregoing description is that of the preferred embodiments of the invention and that various changes and modifications may be made thereto without departing from the spirit and scope of the invention as defined in the appended claims.

What is claimed is:

1. A phase contrast electron microscope defining an optical axis and comprising:

an objective mounted on said optical axis and defining a back focal plane;

a first diffraction lens for imaging said back focal plane into a diffraction intermediate image plane;

a second diffraction lens having a principal plane disposed in the vicinity of said diffraction intermediate image plane; and, a phase-shifting element mounted in or near said diffraction intermediate image plane.

2. The phase contrast electron microscope of claim 1, wherein said objective defines an entrance image plane and images said entrance image plane into an intermediate image plane disposed forward of said diffraction intermediate image plane viewed in beam direction; and, a beam deflection system is mounted in the region of said intermediate image plane.

3. The phase contrast electron microscope of claim 2, wherein said beam deflection system is a double deflection system which deflects an electron beam in two mutually perpendicular directions.

4. The phase contrast electron microscope, of claim 3, wherein said double deflection system effects a sinusoid-shaped beam deflection in a first direction and a cosine-shaped beam deflection in a second direction perpendicular to said first direction so that said electron beam is moved along a circularly-shaped path in a diffraction plane.

5. The phase contrast electron microscope of claim 2, wherein said second diffraction lens images said intermediate image plane into a second intermediate plane; and, wherein said electron microscope further comprises a projective system downstream of said second intermediate plane for imaging said second intermediate image plane magnified into a final image plane.

6. The phase contrast electron microscope of claim 1, further comprising:

an electron source; and, a condenser system having electron lenses for forming an electron beam from the electrons emanating from said electron source.

7. The phase contrast electron microscope of claim 6, wherein said condenser system illuminates an object plane of said objective.

8. The phase contrast electron microscope of claim 1, wherein said electron microscope is operated as a Lorentz microscope with said objective being not excited or only slightly excited.

9. The phase contrast electron microscope of claim 1, wherein said objective defines an entrance image plane; said objective and said first diffraction lens conjointly image said entrance image plane into an intermediate image plane disposed forward of said diffraction intermediate image plane viewed in beam direction; and, a beam deflection system is mounted in the region of said intermediate image plane.

10. The phase contrast electron microscope of claim 1, wherein said phase shifting element is a first phase shifting element; and, further comprising a second phase shifting element mounted in said back focal plane.

11. The phase contrast electron microscope of claim 10, wherein said objective defines an entrance image plane and images said entrance image plane into an intermediate image plane disposed forward of said diffraction intermediate image plane viewed in beam direction; and, a beam deflection system is mounted in the region of said intermediate image plane.

12. The phase contrast electron microscope of claim 11, wherein said beam deflection system is a double deflection system which deflects an electron beam in two mutually perpendicular directions.

13. The phase contrast electron microscope of claim 12, wherein said double deflection system effects a sinusoid-shaped beam deflection in a first direction and a cosine-shaped beam deflection in a second direction perpendicular to said first direction so that said electron beam is moved along a circularly-shaped path in a diffraction plane.

14. The phase contrast electron microscope of claim 10, further comprising:

an electron source; and, a condenser system having electron lenses for forming an electron beam from the electrons emanating from said electron source.

15. The phase contrast electron microscope of claim 14, wherein said condenser system illuminates an object plane of said objective.

16. The phase contrast electron microscope of claim 11, wherein said second diffraction lens images said intermediate image plane into a second intermediate plane; and, wherein said electron microscope further comprises a projective system downstream of said second intermediate plane for imaging said second intermediate image plane magnified into a final image plane.

17. The phase contrast electron microscope of claim 10, wherein said electron microscope is operated as a Lorentz microscope with said objective being not excited or only slightly excited.

18. The phase contrast electron microscope of claim 10, wherein said objective defines an entrance image plane; said objective and said diffraction lens conjointly image said entrance image plane into an intermediate image plane disposed forward of said diffraction intermediate image plane viewed in beam direction; and, a beam deflection system is mounted in the region of said intermediate image plane.

* * * * *

UNITED STATES PATENT AND TRADEMARK OFFICE

CERTIFICATE OF CORRECTION

PATENT NO. : 7,741,602 B2
APPLICATION NO. : 11/717201
DATED : June 22, 2010
INVENTOR(S) : Gerd Benner and Marko Matijevic It is certified that error appears in the above-identified patent and that said Letters Patent is hereby corrected as shown below:

Column 6:
Line 17: delete "n" and substitute -- π -- therefor.

Column 7:
Line 45: delete "microscope," and substitute -- microscope -- therefor.

Signed and Sealed this

Seventh Day of September, 2010

David J. Kappos
*Director of the United States Patent and Trademark Office*